United States Patent [19]

Kienhöfer

[11] 4,431,418

[45] Feb. 14, 1984

[54] DENTAL PROSTHESIS

[76] Inventor: Rolf Kienhöfer, Schubartstrasse 4, D-7326 Heiningen, Fed. Rep. of Germany

[21] Appl. No.: 365,463

[22] Filed: Apr. 5, 1982

[30] Foreign Application Priority Data

Apr. 6, 1981 [DE] Fed. Rep. of Germany ........ 3113817

[51] Int. Cl.³ .......................................... A61C 13/22
[52] U.S. Cl. ..................................... 433/183; 433/206
[58] Field of Search ............... 433/180, 181, 182, 183, 433/206

[56] References Cited

U.S. PATENT DOCUMENTS 4,229,170 10/1980 Perez ................................ 433/206

*Primary Examiner*—Robert Peshock

[57] ABSTRACT

A dental prosthesis formed with a metallic foundation which is structured to include filaments forming a basket-like configuration to support an intermediate core member consisting of a material lighter in weight than the material of the metal foundation and shaped and sized to fill a gap between two adjacent ground teeth upon which the prosthesis is supported. Parts of the surface of the intermediate core member not covered by the filaments of the metal foundation are in direct contact with a ceramic cover layer in the finished prosthesis. The core member may be formed as a prefabricated module with wax filling the parts normally filled by the filaments of the metallic foundation.

7 Claims, 3 Drawing Figures

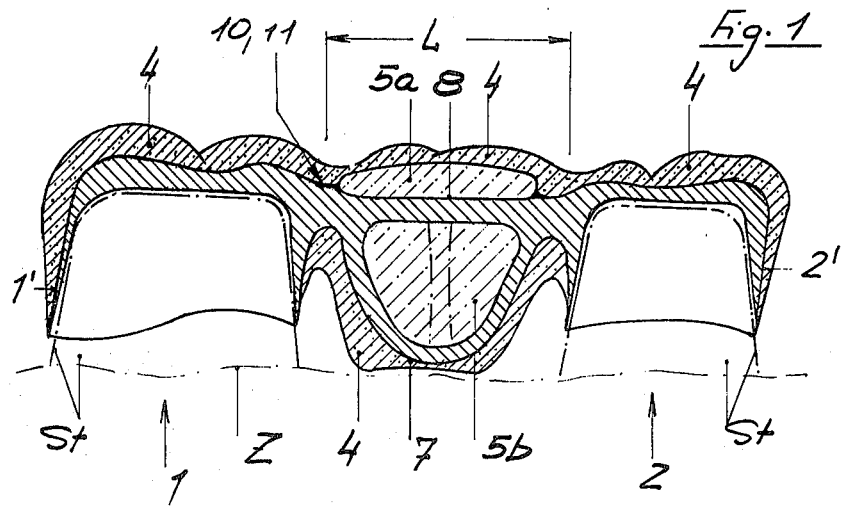
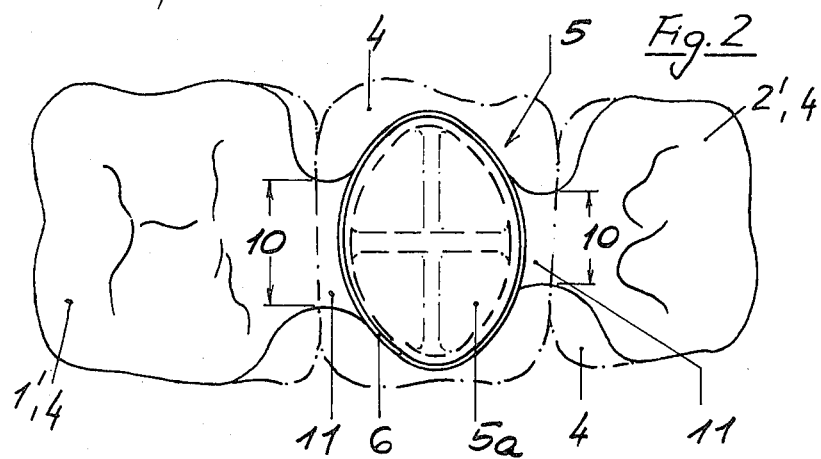
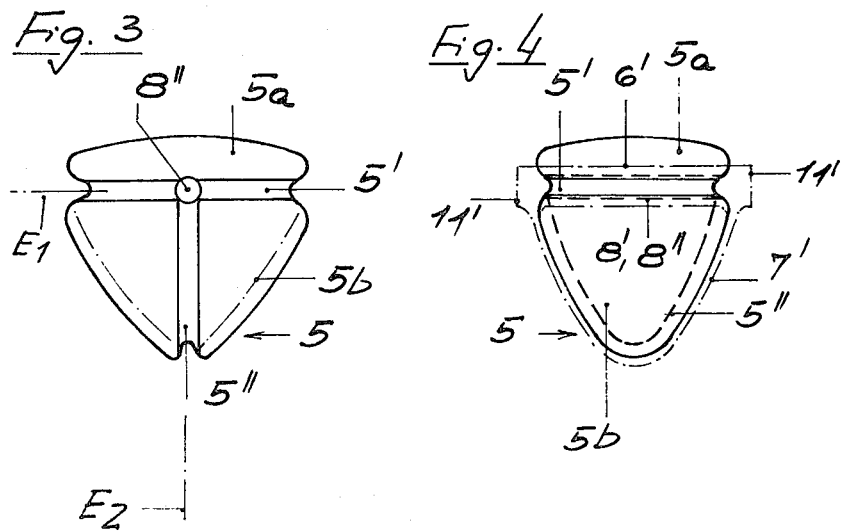

DENTAL PROSTHESIS

The present invention relates generally to dental prosthesis devices and more particularly to a partial denture or tooth replacement structured in the form of a bridge and including a metal foundation with at least two pillars arranged on either side of an intermediate member of the prosthesis. The two pillars engage upon a pair of ground-down teeth and a cover layer of ceramic material or the like is applied to at least partially cover the metal substance.

In devices of the type to which the present invention relates, the metal substance of the bridge member has a core embedded therein and the core may be made of a material which is lighter in weight than the metal substance, for example, it may also be formed of ceramic material.

A bridge member of the type to which the present invention relates is known from German Offenlegungsschrift No. 29 18 124, which discloses a portion of a corresponding denture. In this denture, the ceramic core of the bridge member is completely embedded in the metal foundation and it is completely surrounded thereby. In order to obtain a desired wall thickness for the metal jacket or sheath surrounding the core member, as is required or desired for enabling the casting to be formed during the manufacture of the bridge, support pins must be embedded in the core in order to ensure a necessary gap size.

By utilization of this method, it is possible to manufacture a bridge of lighter weight than would be heretofore available. Furthermore, a certain amount of noble metal, which becomes more and more expensive, may be conserved as compared with bridges formed in accordance with earlier techniques.

However, an approach such as that described above has, in its totality, disadvantages which relate particularly to difficulties encountered during the manufacturing procedure. For example, exact bracing of the core supported in this "floating" manner tends to be extremely difficult and when the parts of such a small size are cast, there usually occurs unequal wall thicknesses. Accordingly, during rough casting or plastering and grinding of the finished cast pieces, it often happens that the metallic wall surrounding the core is ground down beyond a desired depth, thereby causing exposure of the core. This is a particular disadvantage especially when it occurs in areas which are later subjected to relatively high stresses.

A further substantial disadvantage resides in the fact that the support members of the core must be of a material which has a higher melting point than that of the metallic foundation. Accordingly, it becomes necessary not only to operate with extreme caution during separation of the device from the finished cast, but problems also arise due to the necessity for connecting different metals with each other.

The present invention departs from the state of the art in seeking to eliminate the aforementioned disadvantages and to provide a prosthesis wherein the various elements of the prosthesis may be constructed in such a manner that greater conservation of noble metal may be achieved, while simultaneously achieving higher strength and load bearing capacity in the entire prosthesis or bridge.

SUMMARY OF THE INVENTION

Briefly, the present invention may be defined as a dental prosthesis in the form of a bridge comprising a metal foundation including at least two pillars and an intermediate support portion, an intermediate member supported by said intermediate support portion of said metal foundation, and a ceramic cover layer covering said prosthesis, said intermediate member comprising a core member consisting of a material lighter in weight than the material of said metal foundation and having a shape and size corresponding approximately to the shape and size of a gap to be filled between said pillars, said intermediate support portion of said metal foundation being formed in the shape of individual filaments defining a basket-like configuration within which said core member is engaged and supported.

The advantages of the invention are thereby essentially achieved by constructing the bridge so that the non-metallic core corresponds in its initial state approximately to the shape and size of the gap to be closed between the pillars of the bridge and in that the core is connected with the metallic foundation of the prosthesis merely by individual strands or filaments which extend in a basket-like or net-like configuration. Furthermore, the burnt-on ceramic material which serves as the facing or outer cover of the prosthesis or bridge is placed in the region of the bridge member immediately upon those portions of the surface of the core which are free from the metallic strands or filaments of the metal foundation.

Particularly high strength characteristics of the metallic foundation are achieved in that the metal filaments surround and/or extend through the non-metallic core in the manner of tongs and the filaments embrace the lower core portion in the form of a stirrup or similar support member. The individual strands or filaments of the metallic foundation will extend in a plurality of different planes and, in a preferred embodiment of the invention, the metallic filaments are arranged to extend in planes which are perpendicular relative to each other.

In accordance with a further aspect of the invention, in the method for manufacturing the prosthesis, the portions of the core which in the finished bridge would normally be covered or engaged with the metallic filaments of the metal foundation may initially be filled with a wax material in order to form a pattern useful in the casting of the prosthesis. During the casting process, after the wax has melted out, the free surfaces of the core may be immediately placed on the mold walls. This means not only that it is possible to achieve an exact fixing of the core during casting and to obtain perfect castings, but also that the invention, at the same time, provides the facility for the core with the wax strands or filaments and the blocks at the ends of the strands to be formed as a separate finished part. By doing so, such a part may be provided as an industrially prefabricated modular element which comprises a single part useful with any number of shapes of teeth. As a result, such a prefabricated modular part may be universally utilized and may be purchased as a standard stock item by a dental technical laboratory. Clearly, such a capacity contributes significantly to simplification of the production techniques in the formation of dental bridges or prostheses.

Moreover, the net-like or basket-like configuration of that part of the metal foundation which engages and supports the intermediate core member enables control of the thickness of the filaments and provides an especially high degree of saving of noble metal, since it is not necessary to cover the entire outer surface of the core member with metal. This will clearly provide great advantages from the point of view of cost savings, particularly in view of the increasingly higher cost of noble metal. At the same time, the basic strength and load-bearing capacity of the entire prosthesis is undiminished and, in fact, may even be increased.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there is illustrated and described a preferred embodiment of the invention.

DESCRIPTION OF THE DRAWINGS

In the drawings:

FIG. 1 is a sectional view showing a finished prosthesis or bridge structured in accordance with the invention;

FIG. 2 is a top view of the prosthesis shown in FIG. 1;

FIG. 3 is a front view of the core member of the prosthesis of FIG. 1 shown as a separate piece; and FIG. 4 is a side view of the core member shown in FIG. 3.

DETAILED DESCRIPTION OF THE PREFERRED EMBODIMENT

Referring now to the drawings and particularly to FIGS. 1 and 2 wherein like reference characters are utilized to refer to similar parts, there is shown a dental prosthesis formed in accordance with the present invention which is composed of a metal foundation including the metal foundation portions 1' and 2' formed so as to be placed upon or cemented over a pair of ground teeth St thereby to form a pair of pillars 1 and 2 for the prosthesis. The prosthesis is formed so as to avoid pressure upon the gum Z and the teeth St which are part of a set of permanent teeth of a patient wearing the prosthesis have been ground down to accommodate the metal foundation parts 1' and 2'.

When applied in place, the prosthesis serves to close a tooth gap L which is situated between the pillars 1 and 2. In accordance with the invention, the prosthesis or bridge member is formed so as to be composed of a non-metallic core member 5 which may, for example, be of ceramic material.

The core member 5 includes a head portion 5a and a base portion 5b. In accordance with the invention, the core member 5 is retained and supported in place by metallic strands or filaments 6 and 7 of the metal foundation. The filaments or strands 6 and 7 of the metal foundation embrace the core member 5 in such a manner as to form essentially a basket-like or net-like configuration. Thus, the strands or filaments 6, 7 operate in the manner of tongs or a ring in order to support the core 5.

On opposite sides of the core 5, the metal strands 6 and 7 come together in an integral joinder as blocks 11 and in the metal construction they seamlessly continue onto the connecting points 10 of the pillar portions 1', 2'.

As shown in FIGS. 3 and 4, the core member 5 is formed with a first groove 5' within which the filament or ring of the metallic foundation may engage. Also, the core member 5 is formed with a second groove 5" within which the filament 7 engages, the filament 7 thereby being formed in the shape of a stirrup to support the core 5. In addition to the grooves 5' and 5", the core 5 is provided in the head portion 5a with a bore 8" within which another strand or filament 8 of the metallic foundation extends to provide further support for the core 5.

In FIG. 3 there are shown imaginary planes $E_1$ and $E_2$ and it will be seen that the bore 8" and the filament 8 extend at the intersection of these planes. Furthermore, it will be seen that the filament which engages in the groove 5' lies approximately in the plane $E_1$ and that the filament 7 which engages in the groove 5" lies in the plane $E_2$ which extends perpendicularly to the plane $E_1$. Thus, the core is supported in a net or basket of metal strands 6, 7, and 8 which extend, respectively, in the planes $E_1$ and $E_2$, these planes extending perpendicularly relative to each other.

In the final stage of preparation of the prosthesis, so-called burnt-on ceramic material 4 is applied in order to form a facing or protective coating for the entire prosthesis thereby covering virtually all or the essential portions of the prosthesis. The ceramic material 4 is placed in the region of the core member 5 immediately on the free core surfaces 5a and 5b and thereby forms an extremely strong cover and imparts to the entire construction a very high resistance against fracture and a substantial strength while at the same time maintaining low weight characteristics. Additionally, as a result of the overall structure involved, there is substantial saving in the noble metal which must be utilized. In this regard, particularly important for the resistance against fracture of the bridge, is the extremely thick, seamless transition of the strands 6, 7, 8, in the form of blocks 11, to the connecting points 10 of the pillar foundation 1' and 2'.

The core member 5 of the invention may be prefabricated as an individual modular part with wax being applied as a covering particularly in the portions which are ultimately engaged by the metal strands 6 and 7 of the metal foundation. As shown in FIG. 4, the core 5 may be constructed in the shape of a tooth and may be provided as a prefabricated modular part in such a manner that it can be prepared, offered and purchased as a supply part already corresponding to the later noble metal supports 6, 7, 8, and 11 with a wax covering 6', 7', 8', and 11' for placement in a mold or for attaching to the remaining portion of the total wax pattern. This additionally results in significant work simplification for the dental technical laboratory.

Moreover, in this construction in accordance with the invention, exact fixing of the core in the mold is ensured in that the core surfaces at 5a and 5b which are free of wax are braced immediately and immovably against the mold walls.

While a specific embodiment of the invention has been shown and described in detail to illustrate the application of the inventive principles, it will be understood that the invention may be embodied otherwise without departing from such principles.

What is claimed is:

1. A dental prosthesis in the form of a bridge comprising: a metal foundation including at least two pillars and an intermediate support portion; an intermediate member supported by said intermediate support portion of said metal foundation and a ceramic cover layer covering said prosthesis; said intermediate member comprising a core member consisting of a material lighter in weight than the material of said metal foundation and having a shape and size corresponding approximately to the shape and size of a gap to be filled between said pillars; said intermediate support portion of said metal foundation being formed to comprise a plurality of individual filaments defining a basket-like configuration within which said core member is engaged and supported, said core member including recess means within which said individual filaments are engaged to firmly support said core member.

2. A prosthesis according to claim 1 wherein the surface of said core member is only partially covered by said filaments of said metal foundation and wherein said ceramic cover layer is applied to extend into direct contact with portions of said core member not covered by said filaments.

3. A prosthesis according to claim 1 or 2 wherein said core member is formed with an upper head portion and a lower portion and wherein said filaments of said metal foundation surround said upper head portion in the manner of tongs and embrace said lower portion in the manner of a stirrup.

4. A prosthesis according to claim 1 wherein said recess means comprise a bore extending through said core member and wherein said metal foundation is formed with a filament extending into and through said bore.

5. A prosthesis according to claim 3 wherein individual filaments of said metal foundation are arranged to extend in a plurality of different planes, which planes are located to extend transversely relative to each other.

6. A prosthesis according to claim 3 wherein said recess means comprise recessed grooves formed in the surface of said core member, and wherein individual filaments of said metal foundation are arranged to extend within said recessed grooves.

7. A dental prosthesis in the form of a bridge comprising: a metal foundation including at least two pillars and an intermediate support portion; an intermediate member supported by said intermediate support portion of said metal foundation and a ceramic cover layer covering said prosthesis; said intermediate member comprising a core member consisting of a material lighter in weight than the material of said metal foundation and having a shape and size corresponding approximately to the shape and size of a gap to be filled between said pillars; said intermediate support portion of said metal foundation being formed in the shape of individual filaments defining a basket-like configuration within which said core member is engaged and supported, said individual filaments of said metal foundation being connected with said at least two pillars thereof at connecting points located between said pillars and said intermediate support portion, the ends of said filaments surrounding said core member being combined to form a block on each side thereof.

* * * * *